United States Patent
Eryilmaz et al.

(10) Patent No.: US 11,120,672 B2
(45) Date of Patent: Sep. 14, 2021

(54) GARMENT, SYSTEM AND METHOD FOR TRANSMITTING AUDIO AND/OR MESSAGING INFORMATION TO A USER

(71) Applicant: Sanko Tekstil Isletmeleri San. Ve Tic. A.S., Inegol-Bursa (TR)

(72) Inventors: Jitka Eryilmaz, Inegol-Bursa (TR); Ozgur Cobanoglu, Inegol-Bursa (TR); Kadir Ozkan, Inegol-Bursa (TR); Fehim Caglar, Inegol-Bursa (TR)

(73) Assignee: SANKO TEKSTIL ISLETMELERI SAN. VETIC A.S., Inegol-Bursa (TR)

( * ) Notice: Subject to any disclaimer, the term of this patent is extended or adjusted under 35 U.S.C. 154(b) by 0 days.

(21) Appl. No.: 15/876,816

(22) Filed: Jan. 22, 2018

(65) Prior Publication Data

US 2018/0261054 A1 Sep. 13, 2018

(30) Foreign Application Priority Data

Jan. 23, 2017 (EP) ..................................... 17152717

(51) Int. Cl.
*G08B 6/00* (2006.01)
*A61B 5/00* (2006.01)
(Continued)

(52) U.S. Cl.
CPC .................. *G08B 6/00* (2013.01); *A41B 1/08* (2013.01); *A41D 1/005* (2013.01); *A61B 5/6804* (2013.01);
(Continued)

(58) Field of Classification Search
CPC ........... G08B 6/00; A41B 1/08; A41B 5/6804; A41B 2300/35; A41D 1/005; A41D 1/06; A41D 2300/50
(Continued)

(56) References Cited

U.S. PATENT DOCUMENTS 6,422,941 B1 * 7/2002 Thorner .................. A63F 13/02
463/30
8,362,882 B2 * 1/2013 Heubel .................. A41D 1/005
340/407.1
(Continued)

FOREIGN PATENT DOCUMENTS

WO 2016009277 1/2016
WO WO-2016009277 A1 * 1/2016 ......... A41D 13/1281
(Continued)

OTHER PUBLICATIONS

European Search Report dated Jul. 19, 2017 European Priority Application 17152717.9 (withdrawn).
(Continued)

*Primary Examiner* — John A Tweel, Jr.

(57) ABSTRACT

Provided is a garment comprising fabric and at least one seam, said garment comprising at least one vibrotactile actuator configured for producing a vibrational pattern based on audio and/or messaging information provided by an information signal from an external device. The vibrotactile actuator is contained within the seam. Also provided is a system, circuit and method for transmitting audio and/or messaging information to a user. The system comprises the garment, the external device, and a conversion unit comprising a microcontroller that converts the audio and/or messaging information into a driving signal to be provided to the vibrotactile actuator. The circuit comprises the microcontroller and the vibrotactile actuators coupled to one another by a ribbon of a flexible material. The method evaluates the delay between the vibrational pattern produced by the vibrotactile actuator and acoustic and/or visual signals produced by the external device based on the audio and/or messaging information.

22 Claims, 6 Drawing Sheets

(51) Int. Cl.
*A41D 1/00* (2018.01)
*G06F 3/01* (2006.01)
*A41B 1/08* (2006.01)
*A41D 1/06* (2006.01)

(52) U.S. Cl.
CPC .......... *G06F 3/016* (2013.01); *A41B 2300/35* (2013.01); *A41D 1/06* (2013.01); *A41D 2300/50* (2013.01)

(58) Field of Classification Search
USPC ...................................... 340/407.1
See application file for complete search history.

(56) References Cited

U.S. PATENT DOCUMENTS

2011/0063208 A1* 3/2011 Van Den Eerenbeemd ................ G06F 3/011
345/156
2016/0027264 A1* 1/2016 Choi ....................... G06F 3/016
340/407.1
2016/0027338 A1* 1/2016 Ebeling ................ G09B 21/009
340/4.12

FOREIGN PATENT DOCUMENTS

| WO | 2016073802 | 5/2016 |
| WO | 2016128776 | 8/2016 |
| WO | 2017017260 | 2/2017 |

OTHER PUBLICATIONS

International Search Report and written opinion dated Mar. 22, 2018 issued for corresponding PCT application No. PCT/EP2018/051503.
International Preliminary Reprt on patentability dated Aug. 1, 2019 for corresponding PCT/EP2018/051503.
Office Action issued by the European Patent Office dated May 28, 2019 for corresponding EP patent application No. 18152875.3.

* cited by examiner

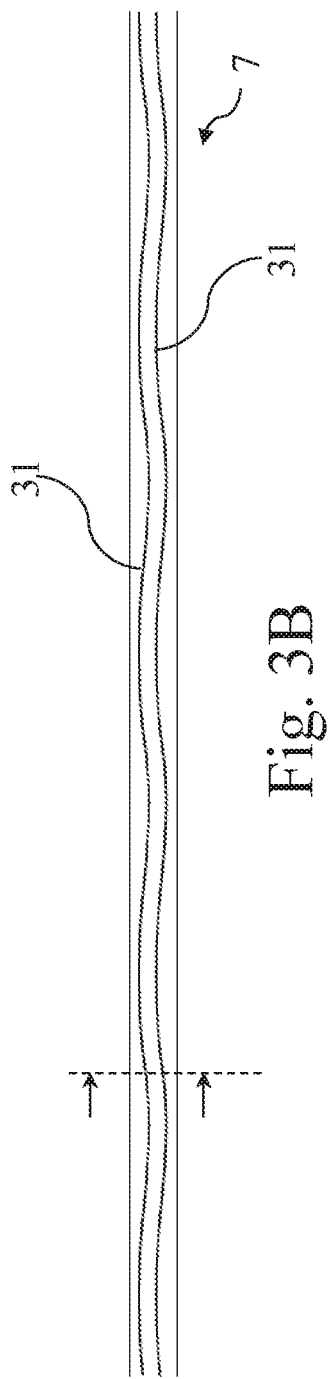
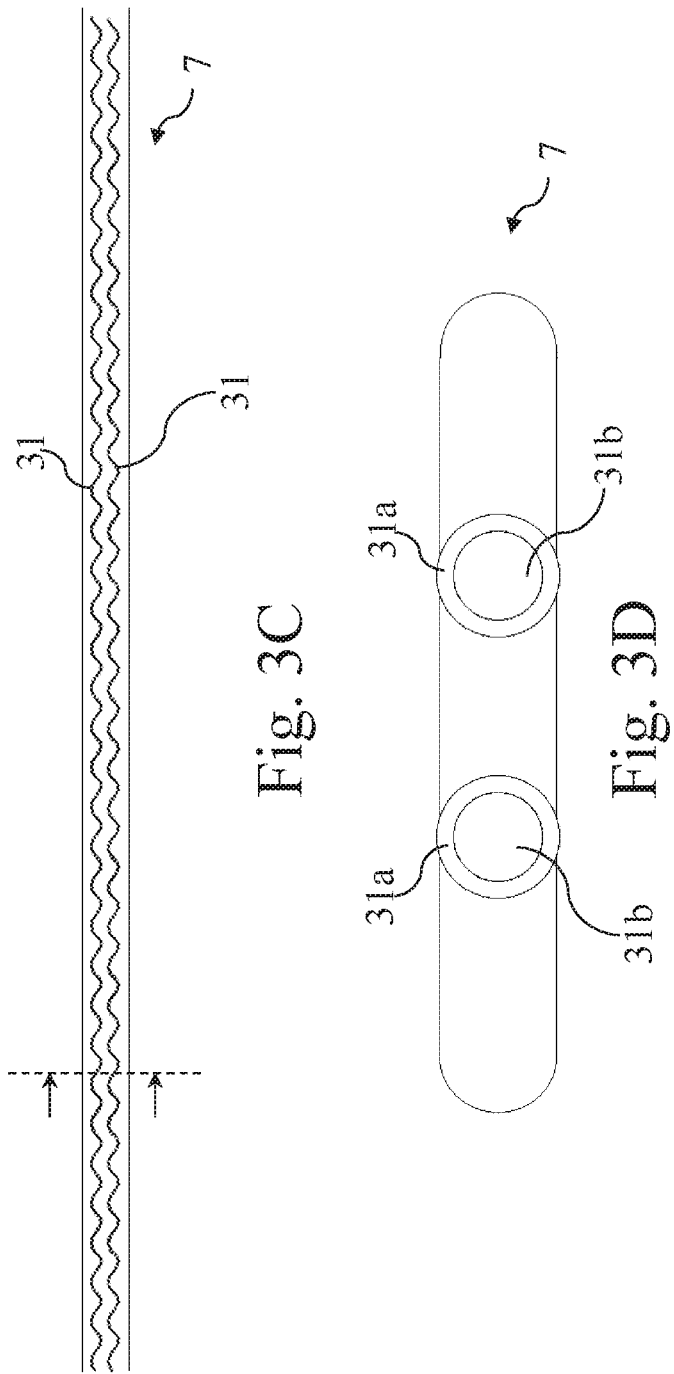
Fig. 3B
Fig. 3C
Fig. 3D

GARMENT, SYSTEM AND METHOD FOR TRANSMITTING AUDIO AND/OR MESSAGING INFORMATION TO A USER

RELATED APPLICATION

This application claims priority to European patent application EP17152717.9, filed Jan. 23, 2017, the contents of which are hereby incorporated by reference as if set forth in their entirety.

TECHNICAL FIELD

The present invention relates to the field of E-textiles (also known as "smart garments"). In particular, the present invention relates to a garment that provides a tactile sensation to a user.

BACKGROUND

Systems for providing a tactile sensation to a user are known. In virtual reality systems, for example, gloves having vibrating units are used for providing to the user a haptic feedback in response to an interaction of the user with the virtual environment.

These gloves are usually provided with one or more vibrating units arranged in correspondence of the user's fingers for transmitting a feedback force to the skin of the user in response to a command signal. For example, vibrating units may include an electric motor having an eccentric mass coupled to its rotating shaft.

Other types of garments, for example sport garments, can be provided with vibrating units. These garments are usually used for providing to the wearer basic information about his physical activity (e.g. an alert about the time limit of the workout) by a vibration. The vibrating units are generally quite visible, relatively heavy, awkward and usually uncomfortable apparatuses designed for short term use.

Improved systems for transmitting more complex information to a user, by using vibrating units, are needed.

SUMMARY OF THE INVENTION

An object of the present invention is to overcome the drawbacks of the prior art cited above and to provide a garment able to provide a tactile sensation to a user that is comfortable to wear and has a stylish appearance.

A further object of the present invention is to provide a system and a circuit for transmitting information to a user by a tactile sensation, that can be easily assembled to a garment in a reliable manner.

A further object of the present invention is to provide a garment and a method for transmitting information to a user by means of a tactile sensation able to enhance the sensorial perception of the user.

These and other objects are achieved by the present invention by means of a garment according to claim 1, by a system according to claim 14, by a circuit according to claim 15, and by a method according to claim 16. Preferred aspects of the invention will be indicated in dependent claims.

In particular, according to the present invention, the garment comprises fabric, at least one seam, and at least one vibrotactile actuator. The vibrotactile actuator(s) being configured for producing a vibrational pattern based on audio and/or messaging information provided by an information signal coming from an external device. According to an aspect of the present invention the one or more vibrotactile actuators (at least one) are contained within the seam(s) of the garment 1.

This aspect advantageously enables the transmission of audio and/or messaging information to the wearer during the daily activity of the user by using a daily garment that is physically comfortable and/or has a stylish appearance.

Advantageously, the at least one vibrotactile actuator is coupled to the garment by a ribbon of a flexible material further arranged within the seam(s) of the garment.

Preferably, the flexible material comprises plastic, textile or conductive yarn. Thanks to the ribbon, the garment according to the present invention can be produced quickly and simply, especially in the case of embodiments provided with a great number of vibrotactile actuators. The ribbon includes a plurality of electrical connections (for example conductive traces, wires or electrical cables) to form a communication bus for the vibrotactile actuators.

Some embodiments provide that the ribbon is elastically stretchable by at least 10% and that the electrical cables are arranged along the ribbon in a crooked path (i.e. a continuously nonlinear path), such as a wavy or a zigzag path. In other words, by applying a determined force at the ends of the ribbon, the ribbon can be stretched (i.e. deformed by increasing its length) by at least 10%. When the force is removed, the ribbon returns elastically to the original size. The wavy or zigzag or crooked pattern of the electrical cables prevent the cables from breaking when the ribbon is stretched.

These embodiments advantageously enhance the wearing comfort, so that the wearer cannot notice the presence of electronics embedded in the garment when the garment is worn.

According to a particular aspect of the present invention, the at least one vibrotactile actuator comprises a shaft-less vibration motor, an ultrasonic actuator, a Linear Resonant Actuator (LRA), a piezoelectric actuator, or a combination of the preceding. The Applicant observed that these type of vibrotactile actuators can be arranged within a seam of a garment in a reliable manner.

Preferably, the garment according to the present invention comprises a plurality of the aforementioned vibrotactile actuators arranged so that the minimum distance (D) between one and another is comprised between about 10 mm and 100 mm. The minimum distance (D) is advantageously chosen on the basis of the wearer's body region to be covered by the garment. In fact, different body regions have different skin resolutions as well as throughput. In other words, by choosing a proper distance (D) within the aforementioned range, the vibration pattern produced by the vibrotactile actuators can be felt by the wearer as a continuous vibrational pattern (for example along a line) without distinguish the position of the single actuators.

According to a further aspect of the present invention, the at least one vibrotactile actuator is controlled by a conversion unit comprising a microcontroller configured for converting the audio and/or messaging information into a driving signal to be provided to the at least one vibrotactile actuator. Preferably, the conversion unit is contained within the at least one seam of the garment. More preferably, the conversion unit comprises a first wireless communication module configured for receiving the information signal from a second wireless communication module of said external device. The first wireless communication module is further configured for providing the audio and/or messaging information to the microcontroller.

Some embodiments provide that the audio and/or messaging information comprise a musical signal. In this case, the driving signal is provided to the at least one vibrotactile actuator for producing a vibrational pattern having substantially the same trend over time with the aforementioned musical signal. For example, the musical signal may be indicative of the amplitude of the driving signal over time.

In the case of an information signal comprising a messaging information, the conversion unit may be configured for providing a driving signal based on a predetermined or customizable code (e.g. the Morse code or the like) in order to provide vibrotactile patterns that the user can decode in a known manner.

According to an aspect of the present invention, the garment comprises a waterproof coating at least on the vibrotactile actuators, within the seam(s) of the garment. This aspect advantageously provides that the electronic components of the garments are isolated from sweat, water and any other liquid or other fluid such as would be experienced during laundering.

Some embodiments can provide that the garment is a pair of pants, preferably formed of denim, or a garment for upper body (such as a t-shirt). In the case of a pair of pants, some embodiments provide that the at least one seam comprises, for each pant leg, an outer lateral seam extending in a longitudinal direction along a wearer's leg and an inner medial seam extending in the longitudinal direction along the wearer's leg. Each of the outer lateral and the inner medial seams comprise one or more of said vibrotactile actuators disposed along a wearer's femur and/or along a lower portion of the wearer's leg. Preferably, the at least one seam of the garment comprises a belt seam extending along a wearer's waist. The belt seam includes at least one of the vibrotactile actuators. In other embodiments the garment may be an upper body garment such as a shirt of various types and models.

Some embodiments can provide that the garment is formed of elastic fabric (for example stretch denim). As a result, when the garment is worn by a user, the vibrotactile actuators are placed substantially at the same distance from the skin of the wearer.

A further object of the present invention is a system for transmitting audio and/or messaging information to a user. The system comprises a garment provided with at least one vibrotactile actuator, an external device configured for providing an information signal containing the audio and/or messaging information, and a conversion unit configured for receiving the information signal and converting the audio and/or messaging information into a driving signal to be provided to the at least one vibrotactile actuator for producing a vibrational pattern based on the audio and/or messaging information. The garment of the system is of the type comprising fabric and at least one seam, wherein the at least one vibrotactile actuator is contained within the at least one seam.

A further object of the present invention is a circuit for transmitting audio and/or messaging information to a user. In particular, the circuit comprises one or more vibrotactile actuators, a microcontroller electrically connected with the vibrotactile actuators, and a communication module adapted to receive an information signal containing the audio and/or messaging information coming from an external device.

The vibrotactile actuators are controlled by the microcontroller for producing a vibrational pattern based on the audio and/or messaging information.

According to an aspect of the present invention, the vibrotactile actuators are coupled to one another by a ribbon of a flexible material comprising a plurality of electrical connections (for example conductive traces, wires or electrical cables) forming a communication bus for the vibrotactile actuators. The flexible material comprises at least one of plastic, textile and a conductive yarn. According to a peculiar aspect of the present invention, the ribbon is conformed to be contained within seams of a garment. As described above, the circuit of the present invention can be mounted within a seam of a garment in a simple and reliable manner.

Some embodiments provide that the ribbon is elastically stretchable by at least 10% and the electrical connections are arranged along the ribbon in a crooked path (i.e. a continuously nonlinear path), such as a wavy or a zigzag path A further object of the present invention is a method for transmitting audio and/or messaging information to a user comprising the step of:
  a) providing a garment comprising at least one vibrotactile actuator;
  b) transmitting an information signal containing said audio and/or messaging information by the external device to the garment;
  c) producing a vibrational pattern based on the audio and/or messaging information by means of the at least one vibrotactile actuator;
wherein the audio and/or messaging information is configured to be produced as acoustic and/or visual signals by the external device. According to an aspect of the present invention, the method comprises the step of d) evaluating the delay between the vibrational pattern produced by the at least one vibrotactile actuator and the acoustic and/or visual signal, and the step of e) producing the acoustic and/or visual signals on the basis of the delay evaluated in the step d) for synchronizing in the time domain the vibrational pattern and the acoustic and/or visual signals.

Some embodiments may provide that acoustic and/or visual signals are produced by the external device with a delay that can be tuned by the user. These embodiments provide a calibration step wherein the step d) is performed by a user. For example, a sample of acoustic and/or visual signals is produced by the external device with a predetermined delay with respect to the vibrational pattern produced by the vibrotactile actuators on the basis of the sample. The user may tune the delay to obtain a "perceived synchronization" between vibrational patterns felt and the acoustic and/or visual signals heard and/or seen. In other words, the user can set the delay to a value that in his opinion corresponds to a synchronization between signals and vibrations; a different user may set the delay to a different value.

A preferred embodiment of the present invention provides that the garment according to any of the preceding aspects above mentioned does not comprise Inertial Measurement Unit (IMU) such as accelerometers, gyrometers, magnetometers, and the like.

BRIEF DESCRIPTION OF THE DRAWINGS

The invention will now be described in greater detail, by way of example, with reference to the accompanying non limiting drawings. It is emphasized that, according to common practice, the various features of the drawing are not necessarily to scale. On the contrary, the dimensions of the various features are arbitrarily expanded or reduced for clarity. Like numerals denote like features throughout the specification and the drawings in which:

FIG. 1A provides an expanded view of a portion of the garment shown in FIG. 1;

FIGS. 3B and 3C show an elastically stretchable ribbon forming a communication bus for the vibrotactile actuators according to various embodiments of the disclosure.

FIG. 3D shows a cross-sectional view of the elastically stretchable ribbons of FIGS. 3B and 3C.

DETAILED DESCRIPTION

Figure 1:
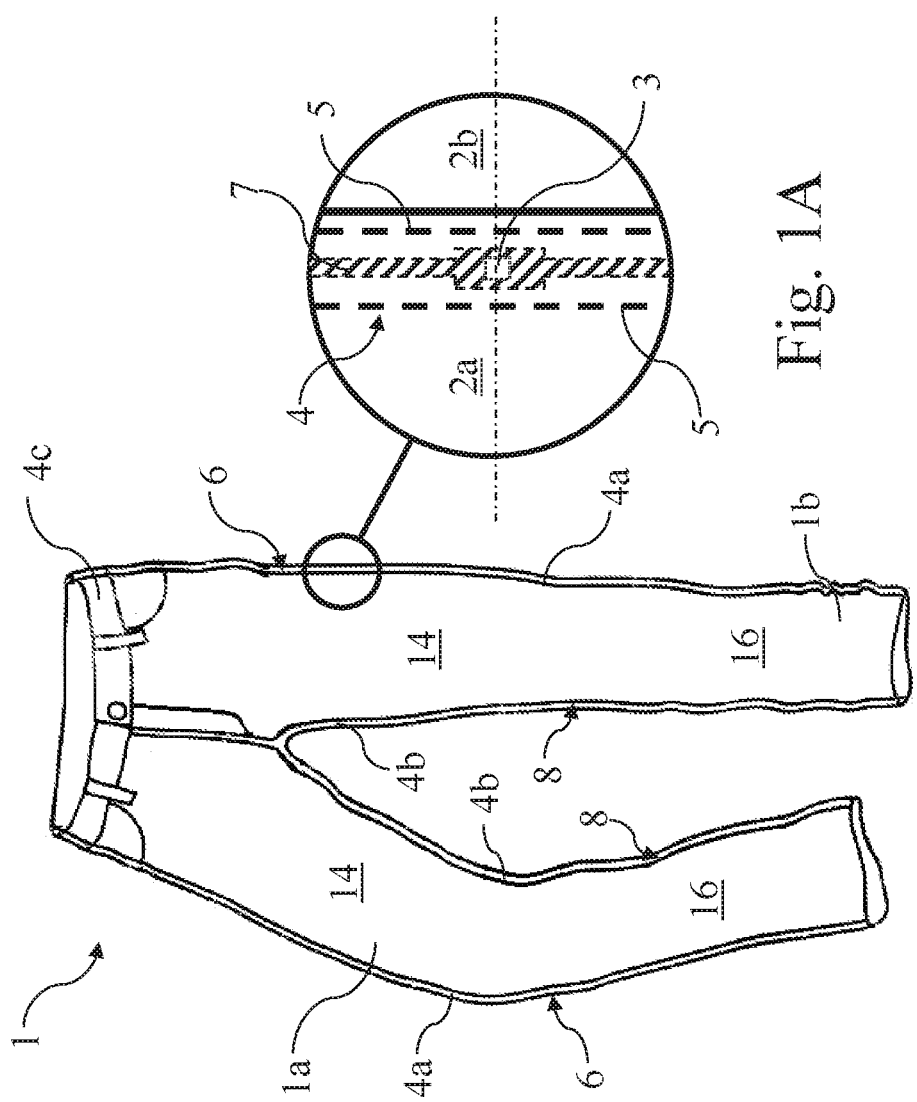
FIG. 1 shows a garment according to various embodiments of the disclosure.

FIG. 1 shows a garment 1 comprising a fabric 2 and at least one seam 4.

Preferably, garment 1 is a pair of pants, but in other embodiments according to various aspects of the present invention, garment 1 may be an item of apparel worn by a wearer including but not limited to shorts, a shirt, a full body suit, sleeves for legs and arms and the like. Garment 1 may be formed of denim, stretch denim or other suitable materials.

With respect to FIG. 1A, garment 1 comprises one or more vibrotactile actuators 3 (shown schematically in dotted line) contained within one or more seams 4 of the garment 1. Vibrotactile actuators 3 are disposed within (i.e. inside) seams 4 and therefore not visible from the outside of the garment 1. Stated alternatively, vibrotactile actuators 3 are surrounded by fabric 2. A seam 4 can be defined as a portion of a garment 1 in which two overlapping portions 2a, 2b of fabric 2 are joined together for example by stitchings 5.

Preferably, the vibrotactile actuators 3 may comprise a shaft-less vibration motor (e.g. a pancake motor), an ultrasonic actuator, a linear resonant actuator (LRA), a piezoelectric actuator, or a combination of the preceding.

Vibrotactile actuators 3 are configured for producing a vibrational pattern based on audio and/or messaging information provided by an information signal coming from an external device 10 such as a smartphone, a computer, a music player or other electronic devices provided with a processor and a communication module for transmitting data to the garment 1. The garment 1 and the external device 10 form a system 100 for transmitting audio and/or messaging information from the external device 10 to a user (shown schematically in FIG. 4) and that will be disclosed with more details in the following of the description herein below.

In other words, the vibrotactile actuators 3 are configured to be in electronic communication with at least one external device 10, preferably by means of a communication system configured to allow the transmission of information signals from the external device to the garment. Vibrotactile actuators 3 are controlled by a conversion unit 33 that converts the audio and/or messaging information to a driving signal (i.e. an electrical signal) with which vibrotactile actuators 3 are actuated.

The audio and/or messaging information may comprise sounds (for example a music) and/or messages (for example phrases, words, emoticons, images) transmitted by the external device 10 to the garment 1 in the form of a digital and/or analogic signals.

Preferably, the information signal comprises for example a RF signal, containing digital data of the audio and/or messaging information, wirelessly transmitted by the external device to the garment 1. Further embodiments can provide that the information signal comprises an electric signal (analogic or digital) containing the audio and/or messaging information, transmitted by means of a wire (for example an audio cable or a USB cable, and the like).

With respect to FIG. 1, seams 4 are preferably arranged at least at outer lateral locations 6 and medial internal locations 8. In the case of a pair of pants, seams 4 are preferably arranged at least at the outer lateral locations 6 and the medial internal locations 8 on each pant leg 1a, 1b. In this case, seams 4 extend along the longitudinal direction of a wearer's legs and are therefore generally parallel to the wearer's femur in upper portion 14 of pant leg 10 and parallel to the wearer's tibia and fibula in lower portion 16 of pant leg 10, when garment 1 is worn by a wearer. In other words, if the garment 1 is a pair of pants, seams 4 preferably comprise, for each pant leg 1a, 1b, an outer lateral seam 4a extending in a longitudinal direction along a wearer's leg and an inner medial seam 4b extending in said longitudinal direction along said wearer's leg. Preferably, each of the outer lateral and the inner medial seams 4a, 4b include one or more vibrotactile actuators 3 arranged along a wearer's femur and/or along a lower portion of the wearer's leg. Further embodiments can provide alternatively or in addition that the garment 1 comprises a belt seam 4c extending along a wearer's waist and including one or more of the vibrotactile actuators 3.

With respect to FIG. 1A, vibrotactile actuators 3 are coupled to the garment 1 by a ribbon 7 of a flexible material further arranged within the seams 4. The flexible material can be preferably formed of plastic, textile or conductive yarn. In some embodiments, vibrotactile actuators 3 are disposed on the ribbon 7 or coupled together by other flexible connectors such as wires, fibers and the like. The ribbon 7 has preferably the form of a long thin ribbon member such as will fit in a conventional garment seam.

In some embodiments, a flexible circuit board such as a kapton board (or "kapton ribbon") is used as ribbon 7 for coupling vibrotactile actuators 3 to the garment 1. Kapton is a polyimide film developed by DuPont in the late 1960s that remains stable across a wide range of temperatures and is commonly used in flexible printed circuits, among other things. In other embodiments, other flexible types of circuit boards and other types of flexible plastic materials and/or flexible insulating materials in ribbon or other form, or various suitable connectors may be used. In other embodiments, ribbon 7 include multiple electrical connections 31 and forming a sort of communication bus. Multiple vibrotactile actuators 3 are coupled to flexible ribbon 7 as will be described in further detail below.

Figure 2:
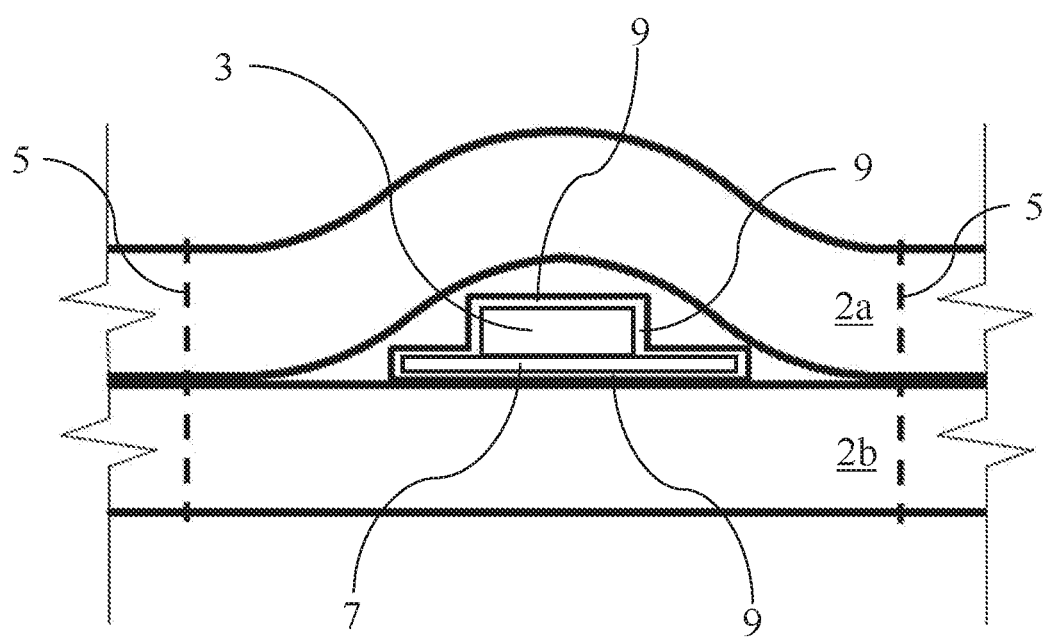
FIG. 2 shows a cross-sectional view of a seam of a garment according to various embodiments of the disclosure.

FIG. 2 shows a cross-sectional view of a seam 4 such as shown in FIGS. 1 and 1A. Vibrotactile actuators 3 and the flexible ribbon 7 are positioned inside seam 4 formed of fabric pieces 2a, 2b. A waterproof coating 9 can be preferably provided on vibrotactile actuators 3 within the seam 4. More preferably, vibrotactile actuators 3 and the ribbon 7 are coated with the waterproof coating 9.

In some embodiments, the ribbon 7 comprises electrical connections 31 (shown in FIG. 3A) so that the ribbon 7 forms a flexible circuit 30 for electrically connecting vibrotactile actuators 3 to each other and/or to the conversion unit 33. In this case, the ribbon 7 is preferably formed of a waterproof material encasing the electrical connections 31 and only the vibrotactile actuators 3 are coated with waterproof coating 9. Various suitable materials such as resin coatings used for isolating electronics or cold molding with materials such as commercially available Acrylonitrile Butadiene Styrene (ABS) resin which is a plastic, may be used as waterproof coating 9. In other embodiments, materials such as other thermoplastics, for example polyamide-6-6, PA66 (i.e. nylon66) may be used. In still other embodiments, other suitable materials may be used as a waterproof coating 9.

Figure 3A:
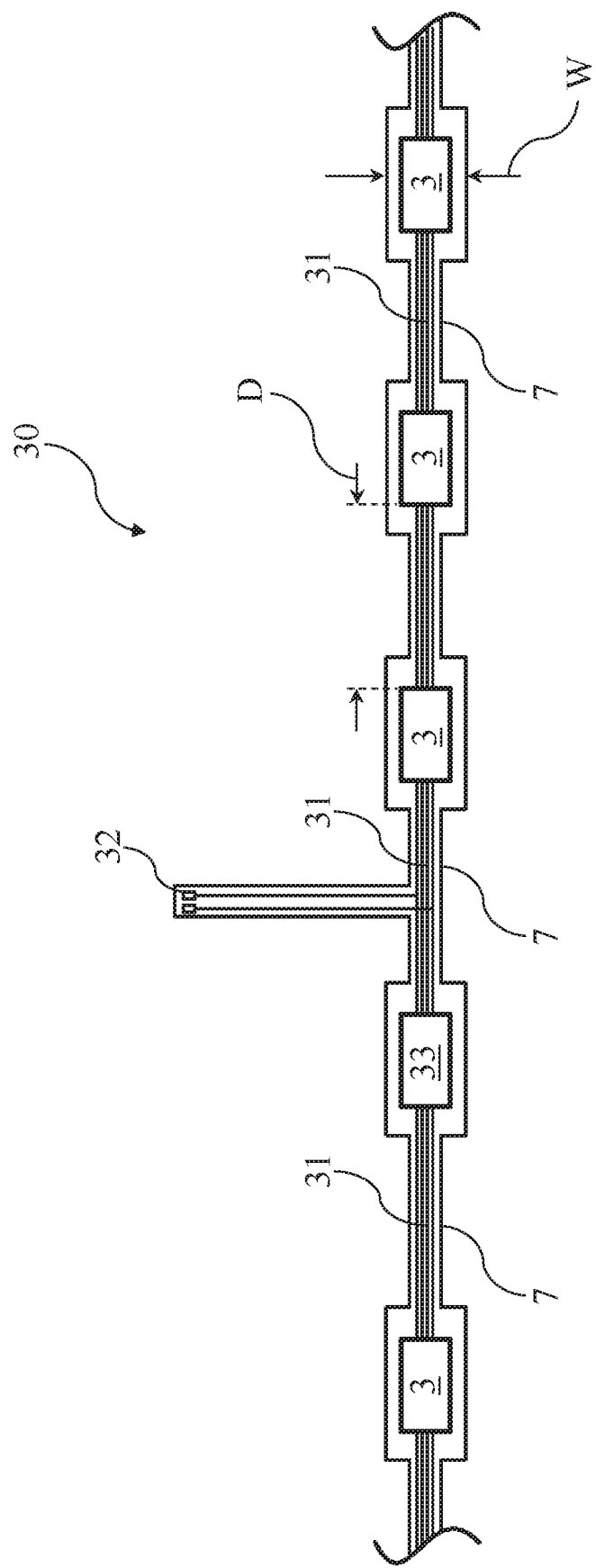
FIG. 3A shows a circuit according to a particular embodiment of the present invention comprising vibrotactile actuators, coupled together by a flexible connector (preferably a ribbon) conformed to be disposed within a seam of the garment according to various embodiments of the disclosure.

With respect to FIG. 3A, it is disclosed a circuit 30, for transmitting audio and/or messaging information from an external device 10 to a user, according to a particular embodiment of the present invention. The circuit 30 comprises a plurality of vibrotactile actuators 3 coupled to the ribbon 7 and a conversion unit 33 configured for converting the audio and/or messaging information contained in the information signal to a driving signal provided to the vibrotactile actuators 3 by the electrical connections 31.

Preferably, ribbon 7 may comprise terminals 32 for electrically connecting the conversion unit 33 to a power source, battery or battery charger. In some embodiments, conversion unit 33 includes a battery that may be a rechargeable battery and according to such embodiments, terminals 32 may provide connection to a battery charger. In some embodiments, terminals 32 may provide connection to a socket (not shown) such as may be positioned outside the seam for connecting the external device 10 to the conversion unit 33 (e.g. by means of an audio cable, or USB cable) so that the information signal can be transmitted from the external device 10 to the conversion unit 33 without the use of RF signals.

In some embodiments, the vibrotactile actuators 3 may be connected to each other by elastically stretchable ribbons 7. In particular, with respect to FIGS. 3B and 3C an elastically stretchable bus comprising a ribbon 7 provided with a couple of electrical cables 31 is shown. The electrical cables 31 are arranged along a crooked path (i.e. a continuously nonlinear path), such as a wavy (undulating) or a zigzag path. The ribbon 7 shown in FIG. 3B has an elastic stretchability less than the stretchability of ribbon 7 shown in FIG. 3C, so that for a given length of the ribbon 7, the electrical cables 31 of FIG. 3C can have a longer length than the embodiment of FIG. 3B. In other words, for a given length of ribbon 7, electrical cables 31 shown in FIG. 3C allow for greater stretching. The electric cables 31 tend to follow a more crooked path in a relaxed position, i.e. in absence of a stretching force, than when a stretching force is applied. In other words, when a stretching force is applied to the ribbon 7, the electric cables 31 follow a path which is more linear in shape, i.e. the electric cables 31 straighten out. In general the ribbon 7 is elastically stretchable by at least 10%. For example, the ribbon 7 may be formed of textile comprising stretchable yarns coupled to the electrical cables 31 by weaving.

Elastic stretchability of the ribbon 7 may be evaluated with the following standards:
ASTM D3107—Stretch Properties of Fabrics Woven from Stretch Yarns;
ASTM D4964—Tension and Elongation of Elastic Fabrics (CRE Tensile Tester);
ASTM D6614—Stretch Properties of Textile Fabrics—CRE Method;
MS P015 Part 1—Extension, Residual Extension of Stretch Woven Fabrics.

Preferably, the standard used for evaluating elastic stretchability of the ribbon 7 is ASTM D3107.

In FIG. 3D a cross-section view of the ribbon 7 shown in FIGS. 3B and 3C is shown. In this embodiment the electrical cables 31 are coaxial cables having an outer conductor 31a and an inner conductor 31b used for providing the driving signal from the conversion unit 33 to vibrotactile actuators 3.

Preferably, vibrotactile actuators 3 are arranged so that the minimum distance D between one and another is comprised between about 10 mm and 100 mm.

Figure 4:
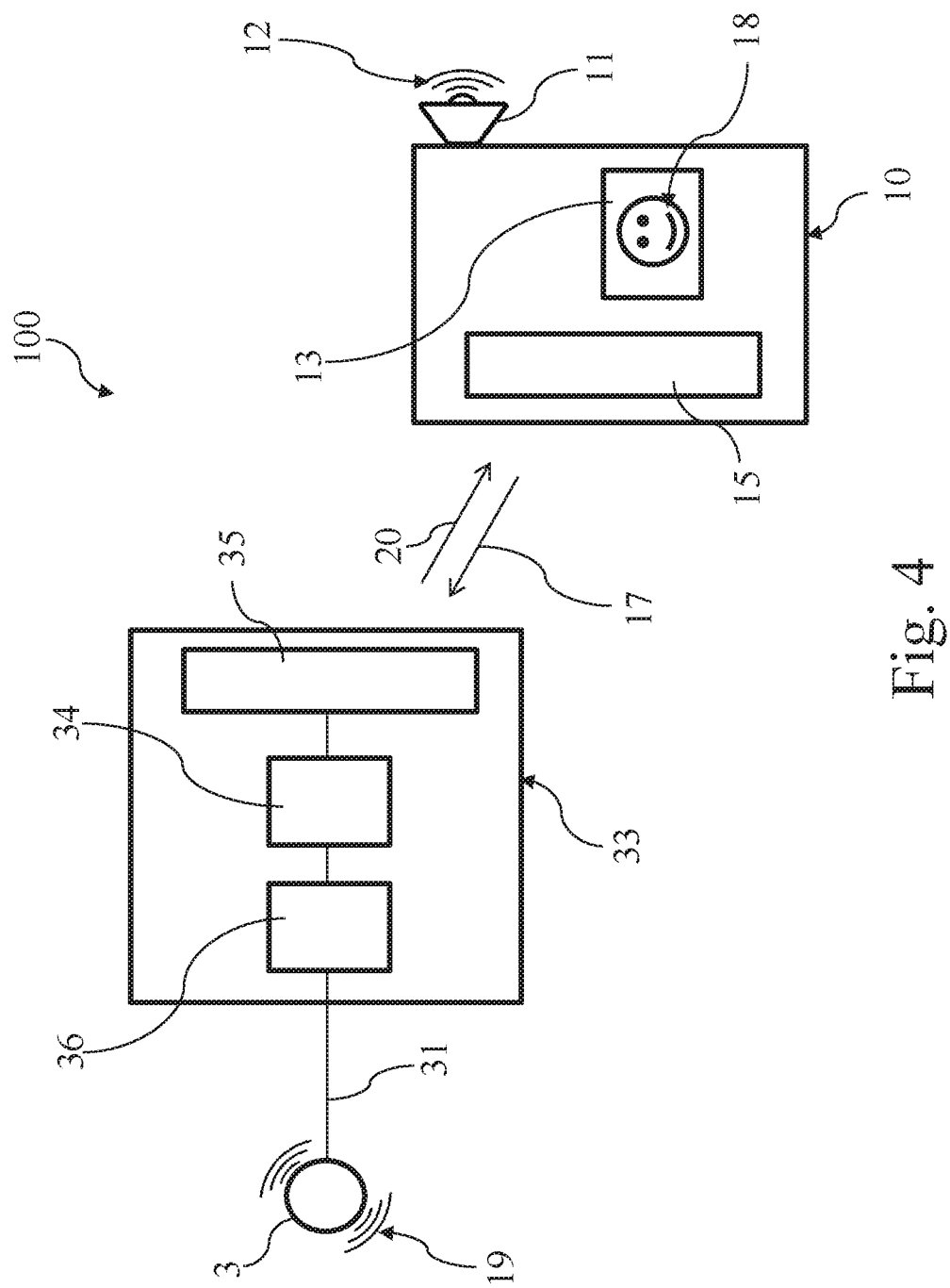
FIG. 4 shows a block scheme of the system according to various embodiments of the disclosure.

FIG. 4 schematically shows the functional blocks of a system 100 for transmitting audio and/or messaging information to a user, according to a particular embodiment of the present invention. In particular, the system 100 comprises the external device 10, the garment 1 provided with one or more vibrotactile actuators 3 contained within the seams 4, and a conversion unit 33 comprising a first communication module 35 and a microcontroller 34. The communication module is configured for receiving the information signal (symbolically indicated as a row 17) and for providing the audio and/or messaging information to the microcontroller 34. The microcontroller 34 is configured for converting the audio and/or messaging information contained in the received information signal 17 into a driving signal (that is an electrical signal) to be provided to the vibrotactile actuators 3 by means of the electrical connection 31. The driving signal is produced by a driving unit 36 (e.g. a D/A converter) so that a vibrational pattern based on said audio and/or messaging information is produced by the vibrotactile actuator 3.

Some embodiments can provide that the communication module 35 may be electrically connected to the terminals 32 for example as shown in FIG. 3. In this case, communication module 35 can be electrically connected to a socket (not shown) configured for receiving the information signal by means of a connection cable for connecting the first communication module 35 of the conversion unit 33 with a second communication module 15 of the external device 10.

For example, in the case of audio and/or messaging information comprising a musical signal, the microcontroller 34 is configured for providing a driving signal so that the vibrational pattern 19 produced by the vibrotactile actuators 3 has substantially the same trend over time with the musical signal. The musical signal can be a digital signal (e.g. a mp3 file, a way file, or other file format) or an analogic signal (e.g. like the output signal of a music player device).

Preferably, in the case of stereo musical signals, the microcontroller 34 may be configured for providing two driving signals for each stereo channel of the musical signal. A first driving signal (right channel) is provided to the vibrotactile actuators 3 of the outer lateral seam 4a of the right pant leg 1a and to the inner medial seam 4b of the left pant leg 1b. The second driving signal (left channel) is provided to the inner medial seam 4b of the right pant leg 1a and to the outer lateral seam 4a of the left pant leg 1b. In this way a hierarchy of stereo data streaming (i.e. leg-seam couples) can be obtained. Some embodiment can provide different hierarchy of stereo data streaming, for example by providing a first driving signal (right channel) to the vibrotactile actuators 3 arranged within the seams 4a, 4b of the right pant leg 1a, and by providing the second driving signal (left channel) to the vibrotactile actuators 3 arranged within the seams 4a, 4b of the left pant leg 1b.

For example, in the case of information signal 17 comprising messaging information, the conversion unit 33 may be configured for providing a driving signal based on a predetermined code (e.g. the Morse code or the like) in order to provide vibrotactile patterns that the user can decode in a known manner Some embodiments may provide that the conversion unit 33 is configured to provide a driving signal based on a personal code customizable by the user, so that messaging information can be decoded and understood correctly only by the user who known the custom code.

Some embodiments may provide that messaging information is pre-analyzed by the external device 10 to recognize the type (phrase, emoticons, images, etc.) of information contained in the messaging information and that the external device 10 sends an information signal 17 to the conversion unit 33 indicative of the type of information. The conversion unit 33 may be configured to provide a driving signal for producing vibrational patterns based on the type of information contained in the information signal. For example, the conversion unit 33 may convert the information signal received from the external device 10 into a driving signal to be provided to vibrotactile actuators located in a region of the garment chosen in function of the type of information received (for example, vibrational patterns associated to emoticons are produced in a determined portion of garment, while vibrational patterns associated to words or phrases in another portion).

Some embodiments may provide that messaging information is pre-analyzed by the external device 10 for recognizing the sender of the message and/or one or more key-words. The key-words to be recognized may be stored in the external device 10. For example, some embodiments may provide that the key-words and/or the senders to be recognized may be selected or chosen by the user. Some embodiments may provide that the key-word to be recognized are stored in a predetermined set and that the user may select and/or modify the set of key-words. These embodiments may provide that the information signal 17 received from the external device 10 contains the key words and/or the sender recognized by the external device 10 and that the conversion unit 33 converts the key-words and/or the sender contained in the information signal into a driving signal for producing vibrational patterns according to a predetermined or a customizable code.

For example, the conversion unit 33 may be provided with a conversion table stored in a memory wherein for each key-word and/or sender a particular vibrational pattern and/or a particular location of the vibrotactile actuators to be driven (i.e. portion of garment) is associated. In other words, the key-words and/or senders to be recognized by the external device 10 are transmitted to the conversion unit 33 for providing a conversion table that associates key-words and/or senders to vibrational patterns according to a predetermined or a customizable code.

With respect to FIG. 4, the external device 10 may be provided with at least one speaker 11 for producing sounds (acoustic waves) or in general acoustic signals 12.

Alternatively or in addition, the external device 10 comprises a display 13 for producing visual signals 18 such as images, symbols, writings, or the like. In general, the external device 10 is provided with means 11, 13 for producing acoustic and/or visual signals based on the audio and/or messaging information sent to the conversion unit 33 of the garment 1.

Preferably, the first communication module 35 is of the wireless type (for example a Bluetooth communication module) configured for receiving the information signal 17 from a second wireless communication module 15 of the external device 10.

Some embodiments can provide that the first and the second communication modules 35, 15 comprise a wireless transceiver for transmitting and/or receiving signals. In this case, the first communication module 35 may transmit an information signal 20 to the second communication module 15 of the external device 10. In this embodiment, signal 20 may contain information about the time delay between the vibrational pattern 19 produced by the vibrotactile actuators 3 and the acoustic and/or visual signals produced by the external device 10.

For example, the microcontroller 34 and the external device 10 may be configured for transmitting and receiving a synchronization signal, as a sort of ping (Packet Internet Groper). Preferably, the microcontroller 34 may be configured to evaluate the time delay between the vibrational pattern 19 produced by the vibrotactile actuators 3 and a synchronization signal (preferably contained in the information signal 17) received from the external device 10. Analogously, the external device 10 may be configured to produce the acoustic and/or visual signals 12, 18 on the basis of the delay evaluated by the microcontroller 34 and transmitted to the external device 10 by the first communication module 35 (preferably, the time delay is transmitted from the conversion unit 33 to the external device 10 by means of the information signal 20). In this way, the external device can produce the acoustic and/or visual signals 12, 18 synchronized in the time domain with the vibrational pattern 19. In the case of musical signal for example the beats of the music will be synchronized with the vibrational pattern 19.

The conversion unit 33 is preferably contained within the seam 4 of the garment 1. In particular the conversion unit may be coupled with the fabric 2 of the garment 1 within the seam 4, or more preferably the conversion unit 33 may be coupled to the ribbon 7 (as shown in FIG. 3).

Some embodiments can provide that part of the conversion unit (for example the communication module and/or the microcontroller 34) or the entire conversion unit 33 may be housed externally the seam 4. For example, the conversion unit 33 may be housed into an electronic button (not shown) configured to be attached in a releasable manner to the garment. In this case, vibrotactile actuators 3 are electrically connected to the conversion unit 33 by means of electric contacts provided on the button and conductive traces provided on the garment 1 as described for example in the European patent application No. 15179147.2 in the name of the same Applicant and having the following title: "Electronic button for smart garments".

Figure 5:
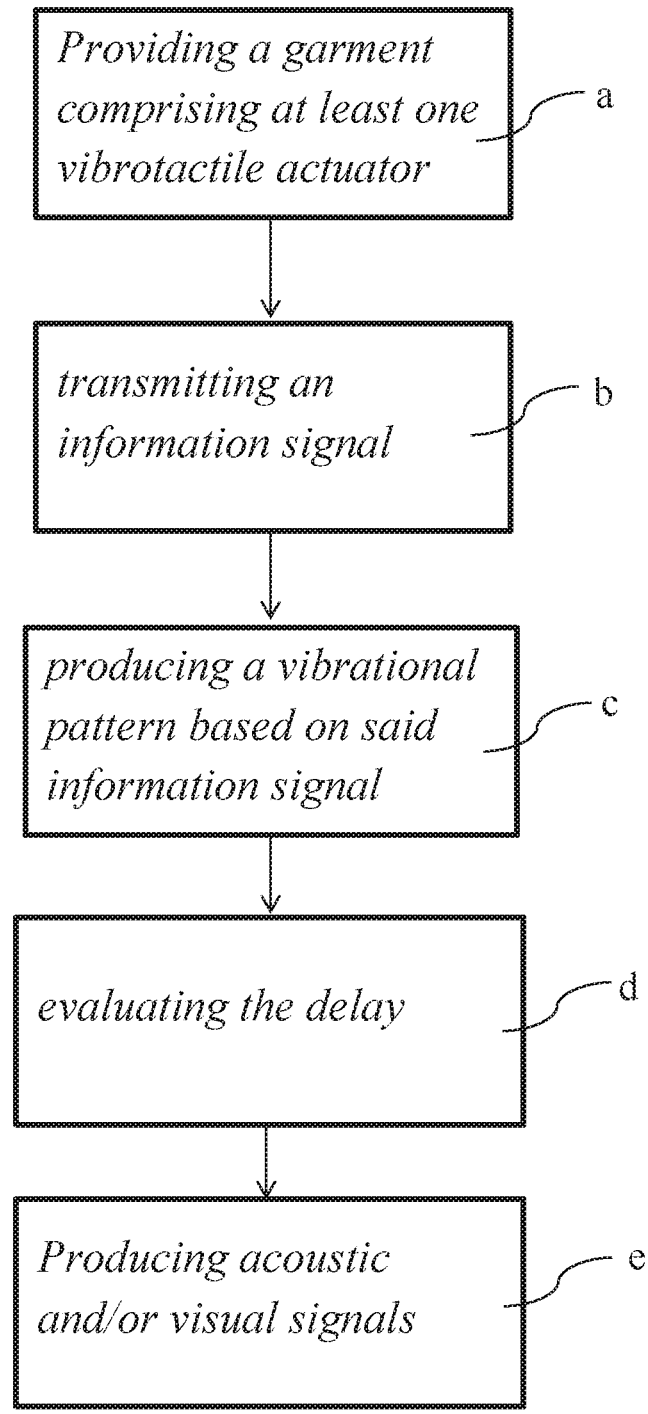
FIG. 5 is a flow chart illustrating a method according to various embodiments of the disclosure.

With respect to FIG. 5, the main steps of a method for transmitting audio and/or messaging information to a user are schematically shown. In particular, the method comprises the steps of:
a) providing a garment comprising at least one vibrotactile actuator;
b) transmitting an information signal 17 containing the audio and/or messaging information from an external device 10 to the garment 1;
c) producing a vibrational pattern 19 based on the audio and/or messaging information by means of vibrotactile actuators 3 of the garment 1.

The external device 10 is configured for producing the audio and/or messaging information as acoustic and/or visual signals. The method may also comprise the further step of:
d) evaluating the delay between the vibrational pattern 19 produced by the vibrotactile actuators 3 and said the acoustic and/or visual signals 12, 18;

Preferably, the method comprises the further step of producing the acoustic and/or visual signals on the basis of the time delay evaluated in the step d), so that the acoustic and/or visual signals produced by the external device 10 are synchronized in the time domain with the vibrational pattern 19 produced by the vibrotactile actuators 3.

Preferably, the evaluation step d) is performed by a user wearing the garment 1. In particular, some embodiments may provide that acoustic and/or visual signals are produced by the external device 10 with a delay that can be tuned by the user.

These embodiments provide a calibration step wherein the evaluation step d) is performed by a user. For example, a sample of acoustic and/or visual signals is produced by the external device 10 with a predetermined delay with respect to the vibrational pattern produced by the vibrotactile actuators on the basis of the sample.

The user may tune, i.e. set, the value of the delay for obtaining a "perceived synchronization" between vibrational patterns felt and the acoustic and/or visual signals heard and/or seen.

In other words, the external device 10 plays, for example, a sample of a sound or of a music, and transmits an information signal 17 containing information about the audio of the sample to the garment, wherein vibrational patterns 19 based on the audio information received are produced by the vibrotactile actuators 3 of the garment. The system (for example by means of the external device 10) asks to the wearer if vibrational patterns felt and the acoustic and/or visual signals heard and/or seen are synchronous.

The delay between vibrational patterns felt and the acoustic and/or visual signals heard and/or seen may be tuned, i.e. set, on the basis of wearer's feedback up to the synchronization perceived by the user is maximized. The above remarks may also be applied, mutatis mutandis, to the processing of a message by the system of the invention.

The invention claimed is:

1. A system (100) for transmitting audio information to a user, said system (100) comprising a garment (1) provided with at least one vibrotactile actuator (3), an external device (10), said external device (10) being provided with at least one speaker (11) for producing acoustic signals and being configured for further providing a non-audible information signal (17) containing said audio information, and a conversion unit (33) configured for receiving said non-audible information signal (17) and converting said non-audible audio information into a driving signal to be provided to said at least one vibrotactile actuator (3) for producing a vibrational pattern (19) based on said non-audible audio information said vibrational pattern being synchronized with said acoustic signal produced by said speaker (11), said garment (1) being of the type comprising fabric (2) and at least one seam (4), wherein said at least one vibrotactile actuator (3) is contained within said at least one seam (4), and is suitable for producing a vibrational pattern (19) based on audio information provided by a non-audible information signal (17) coming from an external device (10), wherein said at least one vibrotactile actuator (3) comprises a shaft-less vibration motor, an ultrasonic actuator (LRA) or a combination of the preceding.

2. A circuit (30) for transmitting audio information to a user, said circuit (30) comprising one or more vibrotactile actuators (3), a conversion unit (33) comprising a microcontroller (34) electrically connected with said vibrotactile actuators (3), and a communication module (35) adapted to receive an information signal (17) containing said audio information coming from an external device (10), said vibrotactile actuators (3) being controlled by the microcontroller (34) for producing a vibrational pattern (19) based on said audio information, wherein said microcontroller (34) is configured for converting said audio information into a driving signal to be provided to said vibrotactile actuators (3), wherein said vibrotactile actuators (3) are coupled to one another by a ribbon (7) of a flexible material, said flexible material comprising at least one of plastic, textile and a conductive yarn, wherein said at least one vibrotactile actuator (3) comprises a shaft-less vibration motor, an ultrasonic actuator, a linear resonant actuator (LRA) or a combination of the preceding and is suitable for producing a vibrational pattern (19) based on audio information provided by an information signal (17) coming from an external device (10).

3. The circuit (30) according to claim 2, wherein said ribbon (7) comprises a plurality of electrical connections (31) forming a communication bus for a plurality of said vibrotactile actuators (3).

4. The circuit (30) according to claim 2, wherein said ribbon (7) is elastically stretchable by at least 10%, said electrical connections (31) being arranged along said ribbon (7) in a crooked path.

5. A method for transmitting audio information to a user comprising the steps of:
   a) providing a garment (1) comprising at least one vibrotactile actuator (3);
   b) transmitting a non-audible information signal (17) containing an audio information by an external device (10) to said garment (1), said external device (10) being provided with at least one speaker (11) for producing acoustic signals;
   c) producing a vibrational pattern (19) based on said audio information by means of said at least one vibrotactile actuator (3);
   wherein said at least one vibrotactile actuator (3) is controlled by a conversion unit (33) comprising a microcontroller (34) configured for converting said audio information into a driving signal to be provided to said at least one vibrotactile actuator (3), and wherein said audio information is configured to be produced as acoustic signals (12) by said external device (10), said at least one vibrotactile actuator (3) comprising a shaft-less vibration motor, an ultrasonic actuator, a linear resonant actuator (LRA) or a combination of the preceding, said at least one vibrotactile actuator (3) being suitable for producing a vibrational pattern (19) based on audio information provided by a non-audible information signal (17) coming from the external device (10), said vibrational pattern being synchronized with said acoustic signal produced by said speaker (11).

6. The method according to claim 5, comprising a calibration step wherein a step of d) evaluating a delay between the vibrational pattern (19) produced by said at least one vibrotactile actuator (3) and said acoustic signal is performed by a user wearing said garment and wherein the delay between the vibrational pattern (19) produced by said at least one vibrotactile actuator (3) and said acoustic signal (12) can be tuned by said user, said method comprising a step of e) producing said acoustic signal (12) on the basis of said delay evaluated in the step d) by said user for synchronizing in the time domain said vibrational pattern (19) and said acoustic signal (12).

7. The system according to claim 1, wherein said audio information comprises a musical signal, said driving signal being provided to said at least one vibrotactile actuator (3)

for producing a vibrational pattern (19) having substantially the same trend over time with said musical signal.

8. The system according to claim 1, wherein said audio information is configured to be produced as an acoustic signal (12) by said external device (10), wherein a delay between the vibrational pattern (19) produced by said at least one vibrotactile actuator (3) and said acoustic signal (12) can be tuned by a user.

9. The circuit (30) according to claim 2, wherein said audio information is configured to be produced as an acoustic signal (12) by said external device (10), wherein a delay between the vibrational pattern (19) produced by said at least one vibrotactile actuator (3) and said acoustic signal (12) can be tuned by a user.

10. A method for transmitting audio information to a user comprising the steps of:
   a) providing a circuit (30) comprising at least one vibrotactile actuator (3);
   b) transmitting a non-audible information signal (17) containing an audio information by an external device (10) to said circuit (30);
   c) producing a vibrational pattern (19) based on said audio information by means of said at least one vibrotactile actuator (3);
   wherein said at least one vibrotactile actuator (3) is controlled by a conversion unit (33) comprising a microcontroller (34) configured for converting said audio information into a driving signal to be provided to said at least one vibrotactile actuator (3), and wherein said audio information is configured to be produced as acoustic signal (12) by said external device (10), said external device (10) being provided with at least one speaker (11) for producing acoustic signals; said at least one vibrotactile actuator (3) comprising a shaft-less vibration motor, an ultrasonic actuator, a linear resonant actuator (LRA) or a combination of the preceding, said at least one vibrotactile actuator (3) being suitable for producing a vibrational pattern (19) based on audio information provided by a non-audible information signal (17) coming from an external device (10), said vibrational pattern being synchronized with said acoustic signal produced by said speaker (11).

11. A garment (1) comprising the system for transmitting audio information to a user according to claim 1.

12. The garment (1) according to claim 11, wherein said at least one vibrotactile actuator (3) is coupled to the garment (1) by a ribbon (7) of a flexible material further arranged within said at least one seam (4).

13. The garment (1) according to claim 12, wherein said flexible material is formed of plastic, textile or conductive yarn.

14. The garment (1) according to claim 13, wherein said ribbon (7) comprises a plurality of electrical connections (31) forming a communication bus for a plurality of said vibrotactile actuators (3).

15. The garment (1) according to claim 14, wherein said ribbon (7) is elastically stretchable by at least 10%, said electrical connections (31) being arranged along said ribbon (7) in a crooked path.

16. The garment (1) according to claim 11, comprising a plurality of said vibrotactile actuators (3) arranged so that the minimum distance (D) between one and another is comprised between about 10 mm and 100 mm.

17. The garment (1) according to claim 11, wherein said conversion unit (33) comprises a first wireless communication module (35) configured for receiving said information signal (17) from a second wireless communication module (15) of said external device (10), said first wireless communication module (35) being further configured for providing said audio information to the microcontroller (34).

18. The garment (1) according to claim 11, wherein said audio information comprises a musical signal, said driving signal being provided to said at least one vibrotactile actuator (3) for producing a vibrational pattern (19) having substantially the same trend over time with said musical signal.

19. The garment (1) according to claim 11, wherein said conversion unit (33) is contained within said at least one seam (4).

20. The garment (1) according to claim 11, comprising a waterproof coating (9) on said at least one vibrotactile actuators (3), within said at least one seam (4).

21. The garment (1) according to claim 11, wherein said garment (1) is a pair of pants.

22. The garment (1) according to claim 21, wherein said at least one seam (4) comprises, for each pant leg (1a, 1b) of said pair of pants, an outer lateral seam (4a) extending in a longitudinal direction along a wearer's leg and an inner medial seam (4b) extending in said longitudinal direction along said wearer's leg, each of said outer lateral and said inner medial seams (4a, 4b) including one or more of said vibrotactile actuators (3) disposed along a wearer's femur (14) and/or along a lower portion (16) of said wearer's leg.

* * * * *